(12) United States Patent
Kang et al.

(10) Patent No.: US 9,798,320 B2
(45) Date of Patent: Oct. 24, 2017

(54) METHOD AND APPARATUS FOR ALARM MONITORING

(71) Applicant: Semiconductor Manufacturing International (Shanghai) Corporation, Shanghai (CN)

(72) Inventors: Randy Kang, Shanghai (CN); Jenny Ma, Shanghai (CN); Elaine Wang, Shanghai (CN); Serena Ji, Shanghai (CN); Chien Wei Ting, Taiwan (CN)

(73) Assignee: Semiconductor Manufacturing International (Shanghai) Corporation, Shanghai (CN)

( * ) Notice: Subject to any disclaimer, the term of this patent is extended or adjusted under 35 U.S.C. 154(b) by 816 days.

(21) Appl. No.: 14/017,297

(22) Filed: Sep. 3, 2013

(65) Prior Publication Data

US 2014/0249656 A1    Sep. 4, 2014

(51) Int. Cl.
*G05B 23/00*   (2006.01)
*G05B 13/02*   (2006.01)
(Continued)

(52) U.S. Cl.
CPC ........ *G05B 23/0235* (2013.01); *A61B 5/0205* (2013.01); *F25J 3/044* (2013.01); *G05B 13/02* (2013.01); *G06F 17/18* (2013.01)

(58) Field of Classification Search
CPC ................................................. G05B 23/0235
See application file for complete search history.

(56) References Cited

U.S. PATENT DOCUMENTS 5,257,206 A * 10/1993 Hanson ................ F25J 3/04303
                                                  700/273
5,555,191 A *  9/1996 Hripcsak ................. G06F 17/18
                                                  340/501

(Continued)

OTHER PUBLICATIONS

Mozumder, P.K.; Shyamsundar, C.R. and Strojwas, A.J., "Statistical Control of VLSI Fabrication Processes: A Framework", May 1988, IEEE Transactions on Semiconductor Manufacturing, vol. 1, No. 2.*

(Continued)

*Primary Examiner* — Mohammad Ali
*Assistant Examiner* — Kelvin Booker
(74) *Attorney, Agent, or Firm* — Kilpatrick Townsend & Stockton LLP (57) ABSTRACT

A method for alarm monitoring abnormal conditions associated with a process operation includes collecting N sample data representing one or more parameters of a process, determining a distribution type of the sample data, obtaining an alarm monitoring strategy associated with the distribution type, and monitoring the process using the alarm monitoring strategy. The distribution type may be single-constant, multi-level discrete, normally distributed, continuous non-normally distributed, cyclical trend-up/down, and drifting away after a period maintenance. The alarm monitoring strategy includes a unilateral or bilateral control chart. The one-side control chart has either an upper control limit (UCL) of (100−p) or a lower control limit (LCL) of (p), and the two-sided control chart has a UCL of (100−p/2) and an LCL of (p/2), where p is a predetermined false alarm rate which determines the number N. The control limit may be a difference between two adjacent sample values of the sample data.

20 Claims, 6 Drawing Sheets

(51) Int. Cl.
G05B 23/02 (2006.01)
A61B 5/0205 (2006.01)
F25J 3/04 (2006.01)
G06F 17/18 (2006.01)

(56) References Cited

U.S. PATENT DOCUMENTS

| | | | | | |
|---|---|---|---|---|---|
| 5,987,398 | A * | 11/1999 | Halverson | ........ | G05B 19/41875 700/275 |
| 6,674,719 | B1 * | 1/2004 | LeComey | ........... | H04M 3/2254 370/235 |
| 6,728,658 | B1 * | 4/2004 | Bechhoefer | ............ | G01H 1/003 702/181 |
| 7,073,198 | B1 * | 7/2006 | Flowers | .............. | H04L 63/1433 713/151 |
| 7,136,794 | B1 * | 11/2006 | Bechhoefer | ............ | G01H 1/003 700/182 |
| 8,057,388 | B1 * | 11/2011 | Russell | .............. | A61B 5/14539 600/300 |
| 8,285,513 | B2 * | 10/2012 | Emigholz | ............ | G05B 13/048 201/1 |
| 8,983,644 | B2 * | 3/2015 | Cheng | .............. | G05B 19/41875 700/100 |
| 2003/0110007 | A1 | 6/2003 | McGee | ............... | G06F 11/0709 702/179 |
| 2003/0225466 | A1 * | 12/2003 | Yulevitch | ............. | G06K 9/6284 700/80 |
| 2004/0030514 | A1 * | 2/2004 | Popp | ................. | A61F 13/15772 702/81 |
| 2004/0083018 | A1 * | 4/2004 | Dollevoet | ......... | A61F 13/15772 700/109 |
| 2005/0210337 | A1 * | 9/2005 | Chester | .............. | G05B 23/0262 714/47.2 |
| 2006/0020423 | A1 * | 1/2006 | Sharpe, Jr. | ........... | C10G 11/187 702/183 |
| 2006/0064291 | A1 * | 3/2006 | Pattipatti | ............ | G05B 23/0243 703/14 |
| 2006/0086172 | A1 * | 4/2006 | Lee | ....................... | G01L 27/007 73/1.88 |
| 2006/0224267 | A1 * | 10/2006 | Higashide | .......... | G05B 23/0235 700/109 |
| 2007/0208519 | A1 * | 9/2007 | Veillette | .................. | G01D 3/08 702/35 |
| 2007/0231933 | A1 * | 10/2007 | Chien | ................. | G05B 23/0232 438/14 |
| 2008/0027677 | A1 * | 1/2008 | Miller | ................ | G05B 19/4184 702/182 |
| 2008/0027678 | A1 * | 1/2008 | Miller | ................... | G05B 23/021 702/182 |
| 2008/0052039 | A1 * | 2/2008 | Miller | ..................... | G05B 17/02 702/182 |
| 2008/0082308 | A1 * | 4/2008 | Kant | .................. | G05B 23/0254 703/12 |
| 2008/0094740 | A1 * | 4/2008 | Lin | ......................... | G11B 27/36 360/31 |
| 2008/0125879 | A1 * | 5/2008 | Miller | .................. | G05B 23/0254 700/30 |
| 2008/0167839 | A1 * | 7/2008 | Miller | .................. | C10G 11/187 703/2 |
| 2008/0177513 | A1 * | 7/2008 | Miller | ..................... | G05B 17/02 703/2 |
| 2008/0188972 | A1 * | 8/2008 | Miller | ................. | G05B 19/4184 700/110 |
| 2009/0198474 | A1 * | 8/2009 | Fritz | ..................... | G01M 15/06 702/183 |
| 2010/0277164 | A1 * | 11/2010 | Tilbrook | ............ | G01R 33/0354 324/244 |
| 2012/0123981 | A1 * | 5/2012 | Graves | .............. | G06F 17/30339 706/13 |
| 2012/0259583 | A1 * | 10/2012 | Noboa | ................... | G05B 15/02 702/179 |
| 2013/0041710 | A1 * | 2/2013 | Civil | ....................... | G06F 17/18 705/7.27 |
| 2013/0226317 | A1 * | 8/2013 | Vijayaraghavan | ..... | G06Q 10/04 700/28 |
| 2013/0262368 | A1 * | 10/2013 | Wolff | ..................... | G06F 17/18 706/52 |
| 2013/0268812 | A1 * | 10/2013 | Liu | ........................ | G05B 13/02 714/57 |
| 2014/0142904 | A1 * | 5/2014 | Drees | ..................... | G06Q 10/04 703/2 |
| 2014/0149325 | A1 * | 5/2014 | Clifton | ................. | A61B 5/0205 706/12 |
| 2015/0227837 | A1 * | 8/2015 | Clifton | ............... | G05B 23/0235 706/52 |

OTHER PUBLICATIONS

Abraham, M.N.; Zain, R.M.; Nopiah, Z.M.; Ghani, J.A.; Deros, B.M.; Mohamad, N. and Ismail, A.R., "Statistical Process Control in SMEs. A Case Study", Oct. 26-28, 2008, 4th WSEAS/IASME International Conference on Dynamical Systems and Control.*
Salzman, K.A., "Statistical Process Control Implementation for GaAs Integrated Circuit Fabrication", 1992, IEEE.*
Scher, G.; Eaton, D.H.; Fernelius, B.R.; Sorensen, J. and Akers, J., "In-Line Statistical Process Control and Feedback for VLSI Integrated Circuit Manufacturing", 1989 IEEE.*
Applied Material, "Data Analytics: Finding What Matters", 2014, Nanochip, vol. 9, Iss 2.*
Bachik, H.; Kamaruddin, S.; Khan, Z.A. and Suhail, A., "A Methodology for Ranking of Alarms in Control Charts", Dec. 2005, Jurnal Mekanikal, No. 20, 52-67.*
Goodlin, B.E.; Boning, D.S.and Sawin, H.H., "Simultaneous Fault Detection and Classification for Semiconductor Manufacturing Tools", May 2002, 201st Meeting of the Electrochemical Society, International Symposium on Plasma Processing XIV, Abs 413.*
Guldi, R.L.; Jenkins, C.D.; Damminga, G.M.; Baum, T.A. and Foster, T.A., "Process Optimization Tweaking Tool (POTT) and its Application in Controlling Oxidation Thickness", May 1989, IEEE Transactions on Semiconductor Manfacturing, vol. 2, No. 2.*
Shyamsundar, C.R.; Mozumder, P.K. and Strojwas, A.J., "Statistical Control of VLSI Fabrication Processes: A Software System", May 1988, IEEE Transactions on Semiconductor Manufactoring, vol. 1, No. 2.*
Spanos, C.J.; Guo, H.-F.; Miller, A. and Levine-Parrill, J., "Real-Time Statistical Process Control Using Tool Data", Nov. 1992, IEEE Transactons on Semiconductor Manufacturing, vol. 5, No. 4.*
Spanos, C.J. and Chen, R.L., "Using Quality Observations for Process Tuning and Control", May 1997, IEEE Transactions on Semiconductor Manufacturing, vol. 10, No. 2.*
Yang, S.F. and Chien, W.T.K., "Effectiveness Indices for Statistical Process Control Chart Performance", 2010, ECS Transactions, 27 (1) 221-226.*
NIST, "Engineering Statistics Handbook", Apr. 2012, Chapter 6.*

* cited by examiner

METHOD AND APPARATUS FOR ALARM MONITORING

CROSS-REFERENCES TO RELATED APPLICATIONS

This application claims priority to Chinese Patent Application No. 201310066956.7, filed Mar. 3, 2013, entitled "Method and Apparatus for Alarm Monitoring", commonly assigned and incorporated herein by reference in its entirety.

FIELD OF THE INVENTION

The present application relates to static process control, and more particularly to a method and apparatus for alarm monitoring in statistical control of processes.

BACKGROUND OF THE INVENTION

During a manufacturing process, product parameters and other specifications may fluctuate due to changes in processing and environmental conditions. Variations of process parameters will affect product quality. Process control techniques can be used to prevent and suppress process parametric fluctuations. Statistical Process Control (Statistical Process Control, referred alternatively as SPC hereinafter) is a technique that relies on statistical process control tools to perform process analysis and evaluation in a manufacturing process. SPC operates based on feedback information to detect systematic parametric variations, and takes appropriate measures to suppress or reduce the impact of parametric variations to ensure that process parameters vary within acceptable ranges.

Statistical control of processes can be implemented in two phases: the analysis phase and the monitoring phase. The analysis phase includes collecting sample data in process operations that have been found to be stable and obtaining control limits of control charts based on the collected sample data. The analysis phase also includes performing analysis using control charts, histograms, and the like. The analysis phase further includes specifying process capability, analyzing whether a process is in a statistical steady-state, and whether the process capability is adequate. The analysis phase also defines the system requirements. If any one of the requirements is not met, the process engineer will investigate the causes of the problems, take corrective actions, readjust the process setup, and restart the analysis. Once control limits of control charts are defined based on the collected sample data, the monitoring phase begins. The main operation of the monitoring phase is to monitor processes using control charts, determines whether the process variables and parameters are within the control limits. In other words, the monitoring phase collects sample data in a production process and determines whether the sample data is within the control limit(s) so as to indicate whether the process is under control or out-of-control. If the process is found to be out of control, the process engineer will investigate the causes and take corrective actions as soon as possible to put the process back under control. The statistical control of processes requires both the analysis and monitoring stages, which may be performed repeatedly, if necessary.

Currently, statistical process control techniques are based on steady state process characteristics that follow a normal distribution, i.e., the sample data can be assumed to fall within plus or minus n times of the standard deviation from a mean value (n is generally equal to 3). If the mean value of a process is steady over time, and n is equal to 3, 99.73% of the sample data is within the control limits. In other words, there is a probability of having a false alarm of about 0.27%. A false alarm is defined as a sample data located outside the control limits.

There is a large number of process parameters in a real manufacturing process. For example, in semiconductor manufacturing, there are multiple process variables of a product, such as film thickness, CD (critical dimension), electrical parameters, yield. There is also a large number of characteristics of machine tools and parameters of the production environment, such as dust quantity, output current (voltage), process time duration, gas flow, pressure, temperature and humidity, and the like. In a real manufacturing environment, data does not behave normally distributed, and some data may not even have a distribution that can be described using mathematical formulas. If a normal distribution-based statistical process control technique is used, false alarms will likely increase the production costs.

As is known, problems frequently arise in a production environment, especially when the production requires a large number of processes. The problems may take the form of malfunctioning equipment, improperly tuned process control loops, and the like. These and other problems generally result in the process operating in an abnormal state. Many statistical process control tools have been developed to determine the causes of the problems and to assist an operator or a maintenance person to correct the problems, once the problems are detected. While these SPC tools are helpful in detecting and correcting problems in a production process, these tools generally require many data samples to generate a control chart. And some of the problems can only be detected after an abnormal situation already exists. Moreover, the data collection and analysis of the data are time consuming and tedious for an operator or a process engineer.

BRIEF SUMMARY OF THE INVENTION

Embodiments of the present invention provide methods, systems, apparatus, and/or computer program products for alarm monitoring in a statistical process control operation that can quickly and accurately determine the control limits of the control charts for the different types of distribution of the sample data.

In an embodiment of the present application, a method for alarm monitoring of a process operation comprises collecting sample data representing one or more parameters of a process, determining a distribution type of the sample data, obtaining an alarm monitoring strategy associated with the distribution type, and monitoring the process using the alarm monitoring strategy.

In an embodiment, the alarm monitoring strategy may be obtained by determining a control limit of a control chart and monitoring the process using the control limit of the control chart.

In an embodiment, the distribution type of the sample data type is determined whether a value level of the sample data is less than a first threshold value. If the value level is less than than the first threshold value, it is determined that the distribution type is a single constant-type or a multi-level discrete type. If the value level is equal to or greater than the first threshold value, the method will determine whether the sample data is normally distributed. If the sample data is not normally distributed, the method will determine whether the distribution type is a continuous non-normal distribution type, cyclical trend-up/down type, or a drift after a periodic maintenance (PM) type.

In an embodiment, determining the distribution type as a single constant-type or a multi-level discrete type may include determining whether the value level is equal to 1. If the value level is equal to 1, the distribution type is a single constant type, and the control limit is equal to a predetermined constant value. Otherwise, the distribution type is determined to be a multi-level discrete type, and the control limit may include an upper control limit and a lower control limit. The upper control limit is set to a maximum value of the sample data, and the lower control limit is set to a minimum value of the sample data.

In an embodiment, determining the distribution type as a continuous non-normally distributed type, cyclical trend-up/down type, or drift after the PM type may include determining whether the distribution of the sample data satisfies PM change conditions. If the distribution type of the sample data does not satisfy the PM change conditions, the distribution type is determined to be a continuous non-normal distribution type. If the sample distribution of the data satisfies the PM change conditions, the distribution type is determined to be the cyclical trend-up/down type or the drift after PM type.

In an embodiment, the method further includes, for the continuous non-normally distributed type, determining whether the control chart is a two-sided (bilateral) control chart having an upper control limit (UCL) and a lower control limit (LCL), where the UCL=(100−p/2) and LCL=(p/2) with p being a predetermined false alarm rate. If the control chart is a one-sided (unilateral) control chart, either UCL=(100−p) percentile, or LCL=(p) percentile.

In an embodiment, if the distribution type is determined to be the cyclical trend-up/down type or a drift after PM type, the control limit of the control chart may include a difference between two adjacent sample values of the sample data according to the following expressions:

$$R = |x_i - x_{i-1}|$$

$$\overline{R} = \frac{\sum R_i}{N}$$

$$UCL = (1 + c \times 0.756) \times \overline{R}$$

wherein $x_i$ is the i-th data in the sample data, N represents the number of the sample data, UCL is the upper control limit, c is an alarm rate adjustment factor. The alarm rate adjustment factor c can be obtained by solving the following equation:

$$1 - p\ \%/2 = \int_0^c \frac{1}{\sqrt{2\pi}} e^{\frac{x^2}{2}} dx$$

wherein p % is a predetermined alarm rate.

In an embodiment, if the distribution type is a continuous non-normally distributed type, a cyclical trend-up/down type, or a drift after PM type, the number of sample data includes at least N sample data, wherein N=2/(p %) with p % being a predetermined alarm rate.

In an embodiment, determining the distribution type may include, if the distribution type is a normal distribution type, and the control chart is a single-sided control chart having either a UCL or an LCL, the UCL or LCL is determined using the following expressions. If the distribution type is a two-sided the control chart having a UCL and an LCL, the control limits of the control chart can be obtained with the following expressions:

$$u = \frac{\sum x_i}{N}$$

$$S = \sqrt{\frac{\sum (x_i - u)^2}{N - 1}}$$

$$UCL = u + c \times S$$

$$LCL = u - c \times S$$

wherein $x_i$ is the i-th data in the sample data, N is the number of the sample data, UCL is the upper control limit, LCL is the lower control limit, c is the alarm rate adjustment factor. The alarm rate adjustment factor c can be solved by the following equation:

$$1 - p\ \% = \int_0^c \frac{1}{\sqrt{2\pi}} e^{\frac{x^2}{2}} dx$$

wherein p % is the predetermined alarm rate.

Another embodiment of the present application provides an apparatus for alarm monitoring of a statistical process control operation. The apparatus comprises a sampling unit that collects N sample data, each of which represents one or more parameters of a process. The apparatus also includes a determining unit, which determines a distribution type of the sample data, an acquisition unit that acquires an alarm monitoring strategy for the distribution type. The apparatus further includes a monitoring unit that monitors the process using the acquired alarm monitoring strategy.

In an embodiment, the number N is a function of a false alarm rate. The number N can also be determined manually or automatically through a lookup table. In another embodiment, the determining unit defines a range and removes sample data (outliers) located outside the defined range. In an embodiment, the alarm monitoring strategy includes a control chart having a control limit. The control limit may be unilateral having either an upper control limit or a lower control limit, the upper control limit may be (1−p) and the lower control limit may be (p), where p is a predetermined false alarm rate. In another embodiment, the control limit may be bilateral having an upper control limit and a lower control limit, where the upper control limit is (1−p/2) and the lower control limit is (p/2), wherein p is the predetermined false alarm rate.

Embodiments of the present application provide many advantages and benefits. One advantage is that, by selecting different control limits associated with the different distribution types of the sample data, a statistical process control method can be quickly established to reduce false alarm probability (FAR, Failure Alarm Ratio) and effective monitoring abnormal fluctuations in the process control of large amounts of data.

The other advantage is, through the automatic determination of the distribution types, an automatic alarm monitoring system can be obtained for selecting the control limits of the control charts associated with the distribution types, the alarm monitoring system thus provides alarms to operators or process engineers in real time.

BRIEF DESCRIPTION OF THE DRAWINGS

The foregoing and further advantages of the present invention will become readily apparent to those of skill in the art from the following detailed description taken in conjunction with the following drawings, in which.

DETAILED DESCRIPTION OF THE INVENTION

It should be noted that the features in embodiments of the present invention may be combined with each other. In the drawings, the same reference numerals refer to the like elements. As used herein, the term "module" or "unit" may be formed of analog circuitry, digital circuitry, or a combination thereof to implement a hardware configuration. The module or unit may also refer to software objects or program instructions or routines that execute in a hardware processing unit. The different modules and units described herein may be implemented to be executed with one or more processing units (e.g., as separate threads) together with a computer readable medium and/or program codes.

In the following, the term "normal distribution" refers to a continuous, symmetrical bell-shaped distribution for variables data that is the basis for control charts for variables. The term "percentile" refers to a value that is obtained by dividing the variables data into 100 equal groups. For example, the kth percentile ($p_k$) is a value such that at least k percent of the observations are at or below this value and (100-k) percent of the observations are at or above this value. The term "sample" refers to a subset of data from a population that can be analyzed to make inferences about the entire population. The term "control limit" refers to a limit that is calculated statistically from collected data. The control limit can be referred to as a lower control limit (LCL) and/or an upper control limit (UCL) on a control chart. They are set at 3-sigma by default. The term "control chart" refers to a graph that has a center line and a UCL and LCL. The control limit is determined by the process itself. The term "target" refers to a desired value for an output characteristic for which process control and alarm monitoring are being applied.

A "continuous type" of numeric data can take on any numerical value such as temperature, thickness, processing time. A discrete type of numeric data means that the data can only have discrete values. Examples of discrete data variables are discrete digital values sampled at discrete time intervals.

Figure 1:
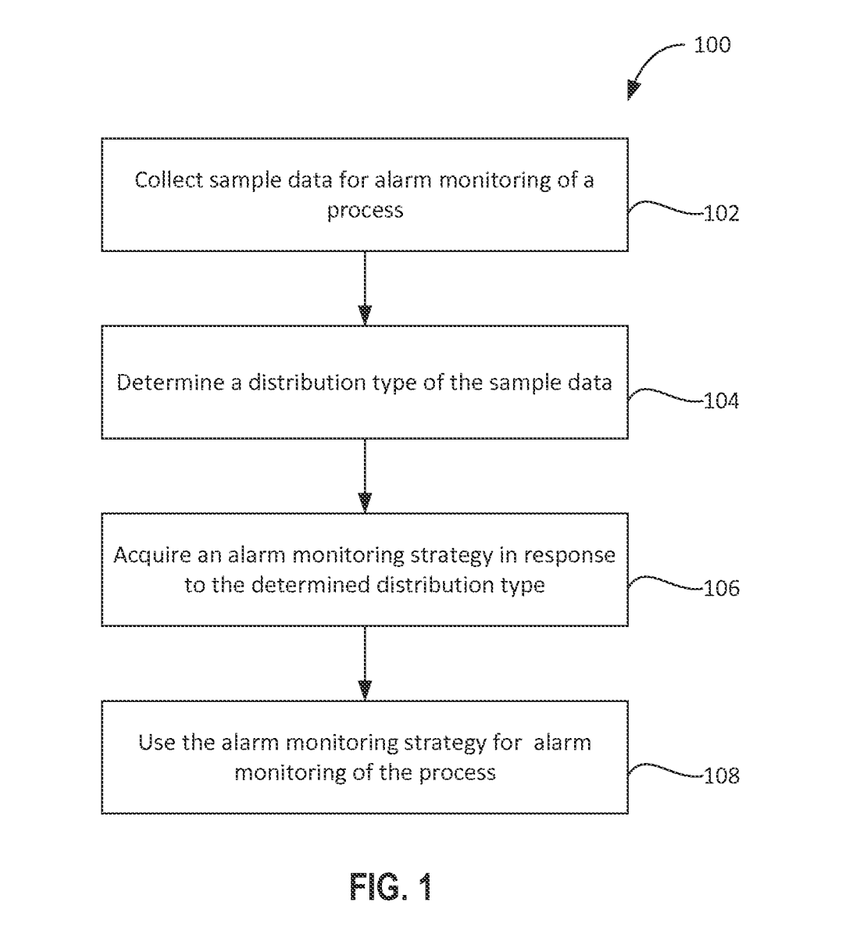
FIG. 1 is a flowchart diagram of a method for alarm monitoring of a process operation according to an embodiment of the present invention.

FIG. 1 is a flowchart diagram illustrating a method 100 for alarm monitoring in a process operation according to an embodiment of the present invention. Method 100 involves collecting sample data in a process at 102.

In some embodiments, the sample data may be represented by different distribution types including, but not limited to, a single constant type (type 1), a multi-level discrete type (type 2), a continuous non-normally distributed type (type 3), a normally distributed type (type 4), a cyclical trend-up/trend-down type (type 5), and a drift after PM (periodic maintenance) type (type 6).

In an embodiment, for the continuous non-normally distributed type, cyclical trend-up/down type, or the drift after PM (periodic maintenance), at least a number N of sample data must be collected in the process for alarm monitoring, where N=2/(p %), and p % is a predetermined alarm rate.

At 104, a distribution type of the sample data is determined. In an embodiment, the distribution type of the sample data can be determined by checking whether a numerical level of the collected data is greater than a first threshold value. If the numerical level is less than the first threshold value, it is determined that the distribution type of the sample data is a single constant-type or a multi-level discrete type. If the numerical level is equal to or greater than the first threshold value, it will be determined whether the sample data is normally distributed. If the sample data is normally distributed, it is determined that the distribution type is a normally distributed type. If the sample data is not normally distributed, it is determined that the distribution type may be one of the continuous non-normally distribution type, cyclical trend-up/down type, or a drift after PM type.

At 106, an alarm monitoring strategy is obtained for the associated distribution type. In an embodiment, the alarm monitoring strategy may be obtained by determining the control limits of the control chart associated with the determined distribution type. If the control chart is a bilateral control chart, the control chart will include an upper control limit and a lower control limit for alarm monitoring. If the control chart is a unilateral control chart, the control chart will include either an upper control limit or a lower control limit for alarm monitoring.

The process for determining the upper and lower control limits of a control chart is described below, where UCL is the upper control limit and LCL is the lower control limit:

For the single-constant type:
UCL=LCL=Target=a predetermined constant.

For the multi-level discrete type:
UCL=maximum constant value (e.g., the maximum value of the sample data),
LCL=minimum constant value (e.g., the minimum value of the sample data),
Target=mean value of the sample data.

For the continuous non-normally distributed type:
Target=the average value of the sample data.

When the control chart is a non-normally distributed and bilateral control chart:
UCL=(100−p/2) percentile,
LCL=(p/2) percentile, where p is a predetermined false alarm rate.

When the control chart is a non-normally distributed and unilateral control chart:
UCL=(100−p) percentile, or
LCL=(p) percentile.

The percentile is described in statistical terms. The term (p) represents a percentile of the total sample data ranging from the smallest value to the largest value, where (p) is the "p" percentage ("p %") of the total number of sample data that is below or at a given UCL value and (1−p %) is the percentage of sample data in the total sample data that is above the UCL value. For example, the total number of collected sample data is 200, and the UCL value is 50, which corresponds to a 70 percentile. That means that 70% of the collected sample data has a value below 50 and 30% of the collected sample data has a value equal to or greater than 50.

For the normal distribution type:
Target=mean value u of the sample data;

$$u = \frac{\sum x_i}{N}$$

$$S = \sqrt{\frac{\sum (x_i - u)^2}{N - 1}}$$

$$UCL = u + c \times S$$

$$LCL = u - c \times S$$

where $x_i$ is the i-th data in the sample data, N is the number of the sample data, UCL is the upper control limit, LCL is the lower control limit, c is the alarm rate adjustment factor. The alarm rate adjustment factor c may be obtained using the following expression:

$$1 - p \%/2 = \int_0^c \frac{1}{\sqrt{2\pi}} e^{\frac{x^2}{2}} dx$$

where p % is the predetermined alarm rate.

For the cyclical trend-up/trend-down type and drift after PM type: the control limit includes the upper control limit for the alarm monitoring. The control limit can be obtained based on a difference between two adjacent data in the collected sample data in accordance with the following expressions:

$$R = |x_i - x_{i-1}|$$

$$\overline{R} = \frac{\sum R_i}{N}$$

$$UCL = (1 + c \times 0.756) \times \overline{R}$$

where $x_i$ is the i-th data in the sample data, N is the number of the sample data, UCL is the upper control limit, c is the alarm rate adjustment factor. The alarm rate adjustment factor c can be obtained by solving the following expression:

$$1 - p \%/2 = \int_0^c \frac{1}{\sqrt{2\pi}} e^{\frac{x^2}{2}} dx$$

where p % is the predetermined alarm rate.

At 108, the process is alarm monitored using the determined alarm monitoring strategy. In an embodiment, using the determined alarm monitoring strategy for alarm monitoring the process comprises using the determined control limit(s) of the control chart.

In the above-described embodiments, through the selection of control limits of the control chart corresponding to different distribution types of the collected sample data, the control limits can be quickly determined for the associated distribution type, so that tedious and time consuming techniques of determining control limits of the prior art can be avoided, and at the same time reduce the false alarm probability and improve the effective monitoring of abnormal fluctuations of large amounts of data.

Figure 2A:
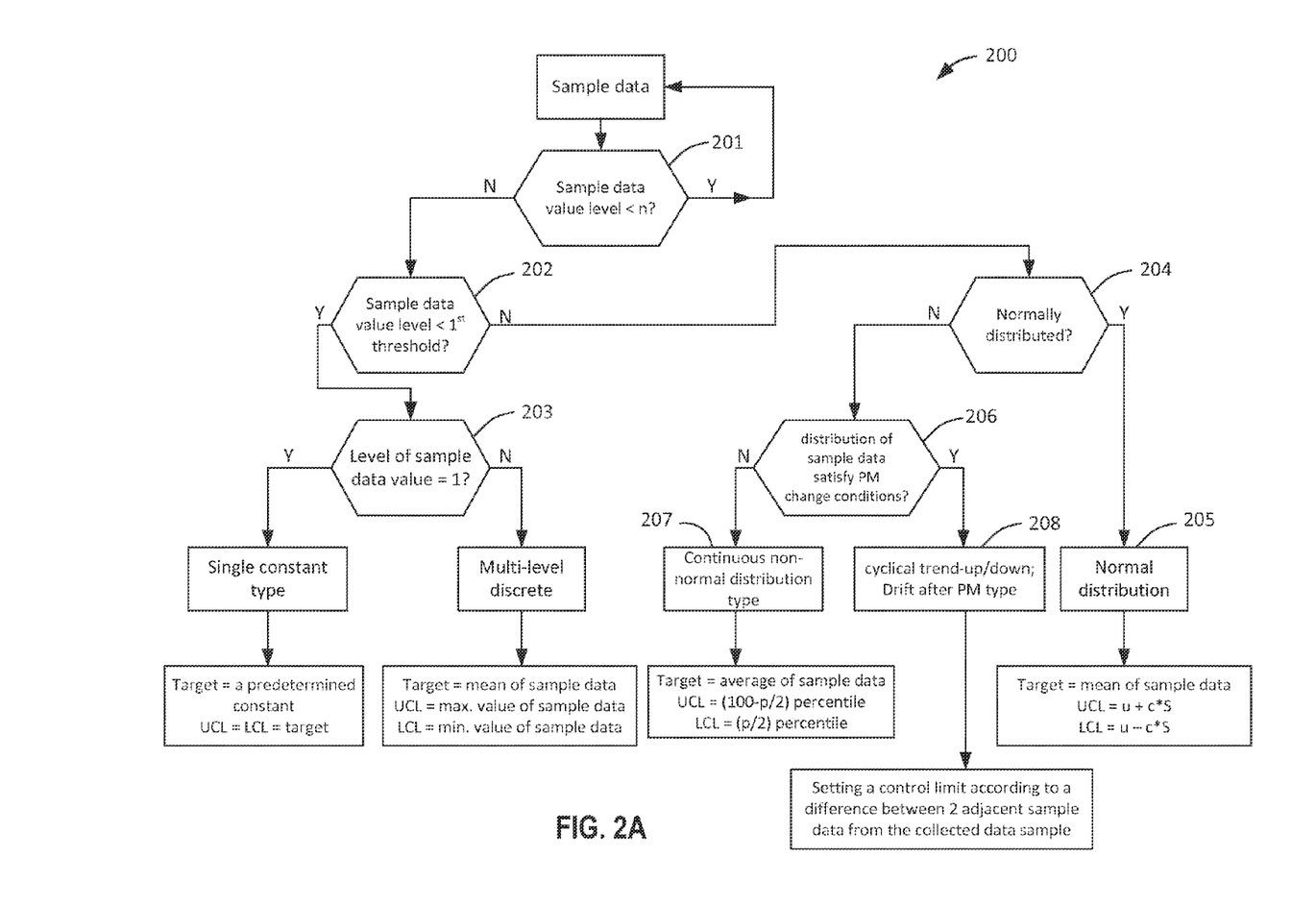
FIG. 2A is a flowchart diagram of a method for alarm monitoring of a process operation according to another embodiment of the invention.

FIG. 2A is a flowchart diagram illustrating a method 200 for determining a distribution type of the collected sample data according to an embodiment of the present invention. As shown, an automatic generation of process quality control chart may include collecting sample data and determining whether the number of collected sample data exceeds a predetermined number n at 201. If the number of the collect sample data is below the predetermined number, process 201 will loop back to sample data until the predetermined number n is exceeded. The predetermined number n can be obtained based on the engineering needs of a given false alarm rate using the following equation:

$$p = 1 + \Phi(\overline{x} - 3*S) - \Phi(\overline{x} + 3*S) \quad \text{Equation (1)}$$

where $$\overline{x} = \frac{t_{1-\frac{\alpha}{2}}(n-1)}{\sqrt{n}}$$

$$S = \sqrt{\frac{(n-1)}{\chi^2_{1-\frac{\alpha}{2}}(n-1)}}$$

$$\Phi(d) = \frac{1}{\sqrt{2\pi}} \int_{-\infty}^{d} e^{\frac{x^2}{2S^2}} dx$$

where:
α is the confidence degree, generally equal to 0.01, 0.05, or 0.1, $$t_{1-\frac{\alpha}{2}}(n-1)$$

is the degree of freedom for the (n–1) of the t-distribution accumulated $$1 - \frac{\alpha}{2}$$

probability values, $$\chi^2_{1-\frac{\alpha}{2}}(n-1)$$

is the degree of freedom for the (n–1) of the chi-square $$1 - \frac{\alpha}{2}$$

distribution accumulated probability values,
S is the standard deviation of the sample data,
$\overline{x}$ is the mean value of the sample data; and
n is the number of sample data.

At 202, the value level (alternatively used for numerical level hereinafter) of the sample data is determined whether the level is less than the first threshold value (in the present embodiment, the value level of the data indicates that the data may be equal to the number of values. For example: If the sample data A=2 or 3, then the numerical level of the sample data A is equal to 2). For example, in an embodiment, the first threshold value is 10, when the value level of the sample data is less than 10, then process 200 proceeds to step 203 to determinate the distribution type between a single-constant type and a multi-level discrete type. If the level of the sample data equal to or greater than 10, then process 200 proceeds to step 204 for continuously distribution monitoring. The above first threshold value of 10 is only an example, which should not unduly limit the scope of the claims herein. One of ordinary skill in the art would recognize other variations, modifications, and alternatives. The first threshold value can be adjusted according to the number of collected data samples.

At 203, the value level of the sample data is determined whether the level is equal to a second threshold. In an embodiment, the second threshold value is equal to 1, this value is used as an example, and the embodiment is not limited thereto. One of ordinary skill in the art would recognize other variations, modifications, and alternatives. The second threshold value can be adjusted according to the number of collected sample data.

When the level of the sample data=1, it is determined that the distribution type of the sample data is a single constant-type (Type 1), the following control limits will be used for process alarm monitoring: UCL=LCL=Target=a predetermined constant.

When the level of the sample data is not equal to 1, it is determined that the distribution type of the sample data is a multi-level discrete type (Type 2), the following control limits will be used for process alarm monitoring: UCL=maximum value (e.g., the max. value of the sample data), LCL=minimum value (e.g., the minimum value of the sample data), Target=the mean value of the sample data.

At 204, the distribution type of the sample data is determined whether it is a normal distribution type. In an embodiment, commercially available test programs may be used to determine whether the distribution of the sample data is a normally distributed type. In addition, different test programs may be used based on different condition requirements. For example, Shipro-Wilk normal distribution test program, D'Agostino test program, AN Kolmogorov test program may be used. For example, if a P value of the test results is greater than 0.05, it is determined that the sample data distribution type is a normal distribution type, and process 200 proceeds to step 205 for a normal distribution type process alarm monitoring. If the P value of the test results ≤0.05, it is determined that the distribution type of the sample data is not a normal distribution type, and process 200 proceeds to step 206 to perform a non-normal distribution control, wherein the P value represents the probability of false positives. The false determination means that the actual distribution of sample data is a normal distribution but the test program falsely determines that the distribution is not a normal distribution. The above described test programs can use commercially available programs and statistical tools.

Figure 2B:
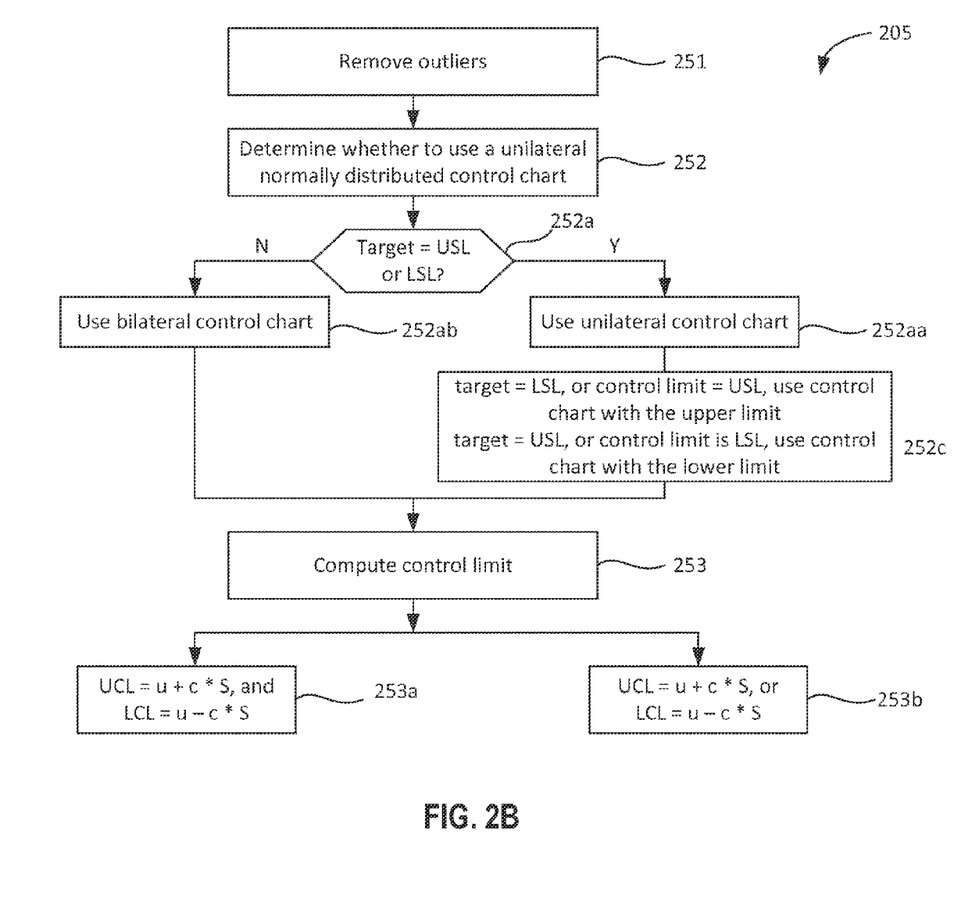
FIG. 2B is a more detailed flowchart diagram of a portion of the method of FIG. 2A.

At 205, the distribution of the sample data is determined to be a normal distribution type (type 4), the following process may be used to perform alarm monitoring. FIG. 2B shows a detail flowchart diagram of step 205. At 251, outliers are removed. Prior to computing the control limits, the outliers in the sample data are removed in order to improve the estimation accuracy. In an embodiment, the determination of outliers of the sample data includes determining whether the sample data is located within the range (Q1−x*IQR, Q1+x*IQR), where Q1 is the 25 percentile, IQR is the difference between the 75 percentile and the 25 percentile, and x is a scaling factor and can be any number such as 1.5, 3, etc. If a sample data is located outside the above range, the sample data is determined as an outlier. In an embodiment, the removal of outliers can be performed automatically using hardware, software, or a combination thereof.

At 252, process 205 determines whether to use a single-sided (unilateral) normally distributed control chart. The normally distributed single-sided control chart can be automatically determined (based on the expected large data or small data) after the removal of the outliers.

At 252a, process 205 determines whether one of the following two conditions is met: 1) only one side of the control chart has a SPEC limit (the upper or lower SPEC limit, referred to as the USL or LSL, respectively); 2) Target is equal to the SPEC limit in either side of the control chart. It is noted that the SPEC limit is provided (or determined) by the customer whereas the control limit is determined by the process itself. The control limit is generally within the SPEC limit.

If one of the above two conditions is met, then the single-side control chart is selected to be used for process alarm monitoring (252aa), otherwise a bilateral control chart is selected to be used (252ab).

At 252c, if there is only USL or Target=LSL, use the unilateral control chart with the upper limit. Conversely, if there is only LSL or Target=USL, use the unilateral control chart with the lower SPEC limit LSL.

At 253, the control limit is calculated.

At 253a, for the bilateral normally distributed control chart, Target=mean value u of the sample, UCL and LCL can be calculated with the following expressions:

$$u = \frac{\sum x_i}{N}$$

$$S = \sqrt{\frac{\sum (x_i - u)^2}{N-1}}$$

$$UCL = u + c \times S$$

$$LCL = u - c \times S$$

wherein $x_i$ represents the i-th data in the sample data, N represents the number of the sample data, UCL is the upper control limit, LCL is the lower control limit, c is the alarm rate adjustment factor, and c may be obtained by solving the following equation:

$$1 - p\% = \int_0^c \frac{1}{\sqrt{2\pi}} e^{\frac{x^2}{2}} dx$$

wherein p % is a predetermined alarm rate.

At 253b, for the unilateral normally distributed control chart, Target=the mean value u of the sample data, u, UCL, LCL can be obtained by the following expressions:

$$u = \frac{\sum x_i}{N}$$

$$S = \sqrt{\frac{\sum (x_i - u)^2}{N-1}}$$

-continued $$UCL = u + c \times S$$

or $$LCL = u - c \times S$$

wherein $x_i$ represents the i-th data in the sample data, N represents the number of the sample data, UCL is the upper control limit, LCL is the lower control limit, c is the alarm rate adjustment factor, and c may be obtained with the following equation:

$$1 - p\% = \int_0^c \frac{1}{\sqrt{2\pi}} e^{\frac{x^2}{2}} dx$$

wherein p % is the predetermined alarm rate.

Referring back to FIG. 2A, at 206, the distribution of the sample data is determined whether or not it satisfies the PM change conditions. Due to periodic maintenance (PM) in a process, the distribution of the collected sample data may satisfy predetermined PM change conditions. In the present embodiment, the collected sample data may include sample data collected in a plurality of process cycles, the PM change conditions may include, but are not limited to, the difference between the mean values of the sample data collected in two adjacent process cycles that is greater than a predetermined threshold value. For example, the mean value of the sample data collected in the first period is 100 and the mean value of the sample data collected in the second cycle is 200. If the difference between the mean values of the sample data in the two adjacent cycles is greater than a predetermined threshold value (e.g., 50), the distribution of the sample data may satisfy the predetermined PM change conditions, or it is determined that there is a shift in the period maintenance (PM shift).

In an exemplary embodiment, the periodic maintenance (PM) may include replacement of chemical solvents in a chemical etching process. Thus, because of the replacement of the chemical solvents, the chemical concentration of the solvents is higher, so that the etching rate suddenly becomes faster, and then with the continuous use of chemical solvents, the chemical concentration of the solvents will become lower, resulting in a reduction of the etching rate as time goes on. The cycle described above can be defined as the time interval between the two adjacent acquisition events of the sample data, for example, when the cycle is equal to 1 hour, the sample data is acquired once every hour.

If the sample distribution of the data does not meet the PM change conditions, the distribution type of the sample data is determined to be a continuous non-normally distributed type (type 3). Otherwise, the distribution type of the sample data is determined to be a cyclical trend-up/down type or a drift after PM type.

Figure 2C:
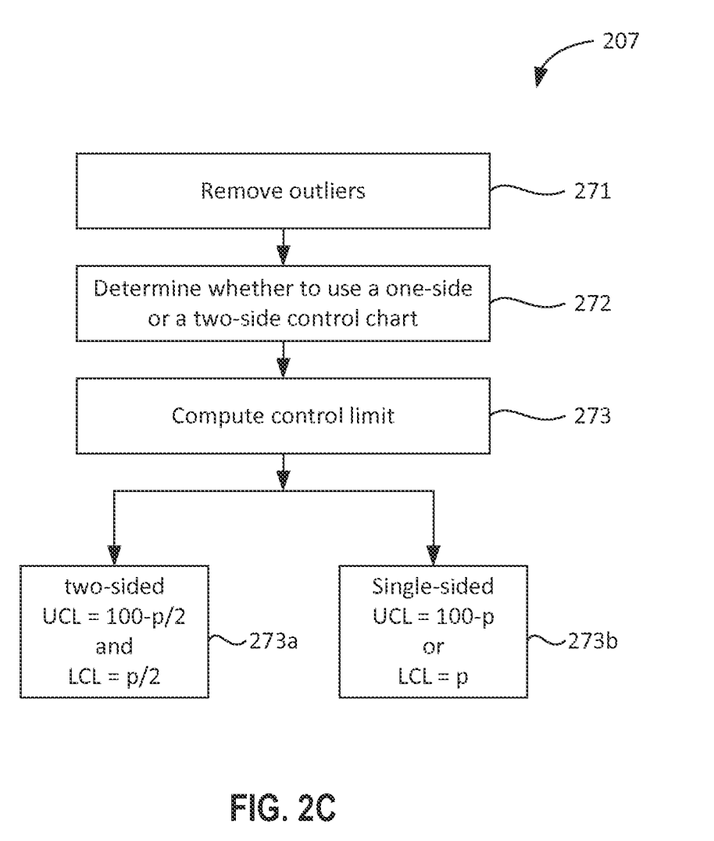
FIG. 2C is a more detailed flowchart diagram of a portion of the method of FIG. 2A.

At step 207, it is determined that the distribution is a continuous non-normally distributed type (Type 3). FIG. 2C is a flowchart diagram illustrating a process 207 for computing the control limits according to an embodiment of the present invention. Process 207 involves removing outliers at step 271. For example, outliers are sample data that have values OOS (out of SPEC) that exceed a predetermined threshold value.

At step 272, it is determined whether to use a single-sided (unilateral) non-normally distributed control chart or a double-sided (bilateral) non-normally distributed control chart. This process step is similar to the process step 252 described above.

At 273, the control limit is calculated. For the control limit of the bilateral non-normally distributed control chart, the upper control limit is the (100–p/2) percentile and the lower control limit is (p/2) percentile (273*a*).

For the control limit of the single-side (unilateral) non-normally distributed control chart, the upper control limit is the (100–p) percentile and the lower control limit is (p) percentile (273*b*).

Referring back to FIG. 2A, at 208, the distribution of the sample data type is determined as a cyclical trend-up/trend-down type (Type 5) or drift after PM type (Type 6). Based on the background setting of the system, the distribution type of the sample data can be determined to be a cyclical trend-up/trend-down type (Type 5) or a drift after PM type (Type 6), a MR (Move Range) control chart can be automatically established, i.e., through the difference (xi–xi–1) of two adjacent sample values. The following formula may be used to calculate the control limit:

$$R = |x_i - x_{i-1}|$$

$$\bar{R} = \frac{\sum R_i}{N}$$

$$UCL = (1 + c \times 0.756) \times \bar{R}$$

wherein $x_i$ is the i-th data in the sample data, N is the number of said sample data, UCL is the upper boundary, c alarm rate adjustment factor. The alarm rate adjustment factor c can be obtained by solving the following equation:

$$1 - p\%/2 = \int_0^c \frac{1}{\sqrt{2\pi}} e^{\frac{x^2}{2}} dx$$

wherein p % of the predetermined alarm rate.

In the embodiment described above, the following processes can be used to select the number of sample data and the false alarm rate. For a non-normal distribution, because most edge is estimated to a (p/2) percentile, so the number of collected sample data is at least the reverse of the estimation of the required percentile, i.e., (2/p %). For example, the predetermined alarm rate is 1%, for the non-normally distributed bilateral control chart the estimated minimum percentile is 0.5%, and it requires at least 200 sample data.

For a normal distribution, due to the estimated parameters of the total collected sample data, the number of sample data may be different, and the estimated error may also be different. Assume that the number of the sample data is n, the mean value of the sample data is $\bar{x}$, the variance of the sample data is $S^2$, the estimated confidence interval for the mean value and for the variance of the sample data is provided by the following formulas [2] and [3].

$\mu$ confidence interval $$[\bar{x} - t_{1-\alpha/2}(n-1)s/\sqrt{n},\ \bar{x} + t_{1-\alpha/2}(n-1)s/\sqrt{n}] \quad \text{Equation (2)}$$

-continued $\sigma^2$ confidence interval $$[(n-1)s^2/\chi^2_{1-\alpha/2}(n-1), (n-1)s^2/\chi^2_{\alpha/2}(n-1)] \quad \text{Equation (3)}$$

where:
α is a confidence level, generally equal to 0.01, 0.05, or 0.1;

$$\chi^2_{1-\frac{\alpha}{2}}(n-1)$$

is a degree of freedom for the (n−1) of the chi-square distribution of the cumulative probability of the (1−α/2) value; $t_{1-\alpha/2}$ (n−1) is a degree of freedom for the (n−1) of the cumulative probability of the (1−α/2) value;
S is the standard deviation of the sample data;
$\bar{x}$ is the number of sample data; and
n is the number of sample data.

Figure 3:
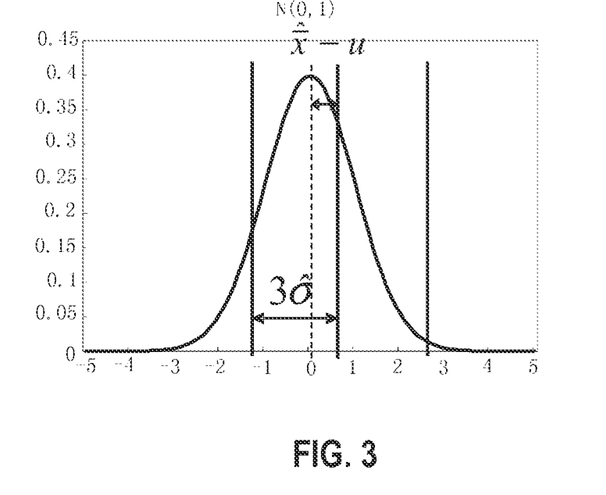
FIG. 3 is a graph of a distribution curve of the sample data according to an embodiment of the present invention.

From the above formulas, it can be seen from the estimated mean deviation of the overall mean value, the variance of the estimate is less than the overall variance, as shown in FIG. 3. After normalization, the estimated mean is $\hat{\mu}$ and the estimated variance is $\hat{\sigma}^2$, therefore, use the confidence interval estimate (1−α) (where α is generally selected to be 0.05), and take into account that the maximum of the estimated mean is $\hat{\mu}_{max}$, when the minimum of the estimated standard deviation is $\hat{\sigma}_{min}$, the alarm rate is maximum. Therefore, the false alarm rate p is a function of the number of sample data, and the function is provided by formulas [2] and [3]. The number of the collected sample data can be calculated given the false alarm rate p, confidence degree α (Alpha), and the required WECO rule are known. In an embodiment, the number of the collected sample data can be selected from following Table 1.

Table 1 shows the number of sample data as a function of a false alarm rate for different values of Alfa and WECO rules. The WECO rules (Western Electric) rules are decision rules for detecting out-of-control or non-random conditions on control charts. The WECO rules ensure that process engineers and maintenance operators interpret control charts in a uniform way.

For example, in accordance with Table 1, for a WECO 2 rule, Alpha=0.05, and the false alarm rate of 1%, the minimum number of sample data is 200. And for a WECO 2 rule, Alpha=0.01, and the false alarm rate of 1%, the minimum number of sample data is 400.

Therefore, in order to make the rate of false alarms in the control chart of the normal distribution and non-normal distribution to be less than 1%, the number of collected sample data is at least 200 for Alpha=0.05. In an embodiment, if the calculated minimum number of the sample data obtained by solving the equations (1) through (3) and the minimum number of sample data obtained through the look-up table (Table 1) is not the same, then select the larger number of the two as a minimum number for the collected sample data.

The processes described above in FIGS. 1 through 3 can be implemented in hardware, firmware, software, or any combinations thereof. The implementation can be an electronic circuit or a computer program stored in a computer or machine readable storage medium that is executable by a processing unit. The computer program can be written in any form of programming languages.

Figure 4:
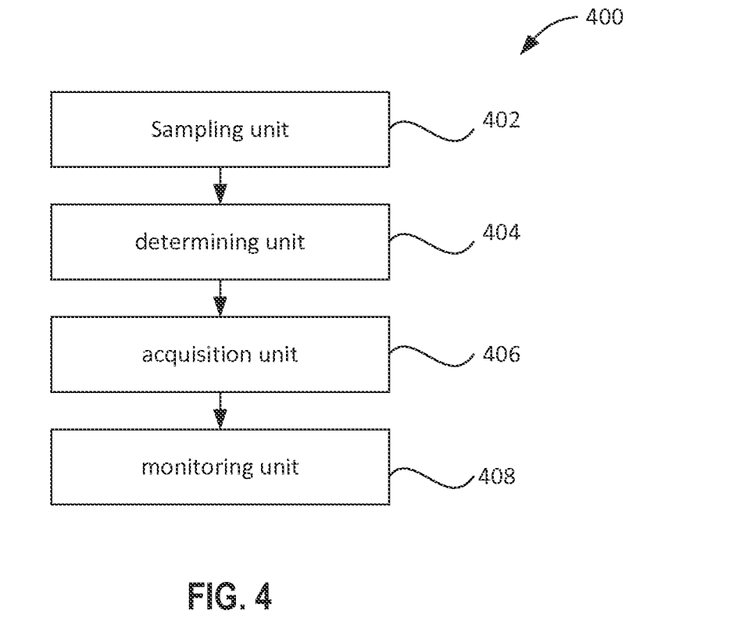
FIG. 4 is a simplified block diagram of an alarm monitoring apparatus according to an embodiment of the present invention.

FIG. 4 is a simplified block diagram of an alarm monitoring apparatus according to an embodiment of the present invention. As shown, the alarm monitoring apparatus includes a sampling unit 402, a determining unit 404, an acquisition unit 406, and a monitoring unit 408.

In an embodiment, sampling unit 402 is configured to obtain or collect sample data in a production process to monitor the production process and send alarms to an operator if the sample data is determined to be out of a control limit. In an embodiment, sampling unit 402 can obtain or collect the sample data automatically without any involvement of an operator and stored the sample data in a system memory (not shown). In an embodiment, the sample data may include, but not limited to, following distribution types: a single constant-type (Type 1), a multi-level discrete-type (Type 2), a continuous non-normality type (Type 3), a normal distribution (type 4), a cyclical trend-upward/downward type (Type 5) and a drift after a PM type (Type 6).

In an embodiment, for the continuous non-normal distribution type, cyclical trend-up/down type, or the draft after

TABLE 1

| | Alpha | | | | | | | | |
|---|---|---|---|---|---|---|---|---|---|
| | 0.1 | | | 0.05 | | | 0.01 | | |
| n | 1 rule | 2 rule | 3 rule | 1 rule | 2 rule | 3 rule | 1 rule | 2 rule | 3 rule |
| 10 | 9.2% | 9.4% | 9.6% | 13.5% | 13.8% | 14.0% | 27.0% | 27.2% | 27.4% |
| 20 | 3.8% | 4.0% | 4.3% | 5.2% | 5.5% | 5.7% | 9.4% | 9.6% | 9.9% |
| 30 | 2.5% | 2.7% | 3.0% | 3.3% | 3.5% | 3.8% | 5.5% | 5.8% | 6.0% |
| 40 | 1.9% | 2.2% | 2.4% | 2.4% | 2.7% | 3.0% | 3.9% | 4.2% | 4.5% |
| 50 | 1.6% | 1.8% | 2.1% | 2.0% | 2.3% | 2.5% | 3.1% | 3.4% | 3.6% |
| 80 | 1.1% | 1.4% | 1.7% | 1.4% | 1.6% | 1.9% | 2.0% | 2.2% | 2.5% |
| 100 | 1.0% | 1.2% | 1.5% | 1.2% | 1.4% | 1.7% | 1.6% | 1.9% | 2.2% |
| 200 | 0.7% | 0.9% | 1.2% | 0.8% | 1.0% | 1.3% | 1.0% | 1.3% | 1.5% |
| 300 | 0.6% | 0.8% | 1.1% | 0.6% | 0.9% | 1.2% | 0.8% | 1.1% | 1.3% |
| 400 | 0.5% | 0.8% | 1.1% | 0.6% | 0.8% | 1.1% | 0.7% | 1.0% | 1.2% |
| 500 | 0.5% | 0.8% | 1.0% | 0.5% | 0.8% | 1.1% | 0.6% | 0.9% | 1.2% |
| 800 | 0.4% | 0.7% | 1.0% | 0.5% | 0.7% | 1.0% | 0.5% | 0.8% | 1.1% |
| 1000 | 0.4% | 0.7% | 0.9% | 0.4% | 0.7% | 1.0% | 0.5% | 0.8% | 1.0% |

PM, the number of sample data collected in a production process for the alarm monitoring data includes at least N samples, where N=2/p %, and p % is a predetermined alarm rate.

Determining unit 404 is configured to determine the distribution type of the sample data. In an embodiment, determining unit 404 determines whether a value level of the sample data is greater than a first threshold value. If the value level is less than the first threshold value, it is determined that the distribution type is a single constant type or a multi-level discrete type. If the numerical level is equal to or greater than the first threshold value, determining unit 404 determines whether the sample data is a normal distribution type. If the sample data is determined to be normally distributed, the distribution of the sample data is a normally distributed type (205). If the sample data is not normally distributed, the distribution type is determined to be either a continuous non-normal distribution type, cyclical trends-up/down type, or a drift after the PM type (206).

The determination of the different distribution types can be performed either by hardware, firmware, software, or a combination thereof according to the flow chart shown in FIG. 2. Further description will not be provided for the sake of brevity.

Acquisition unit 406 is configured to obtain an alarm monitoring strategy associated with the determined distribution type. In an embodiment, obtaining the alarm monitoring strategy comprises determining the control limit of the control chart associated with the distribution type. If the control chart is two-sided (bilateral), the control limit includes an upper control limit and a lower control limit. If the control chart is one-sided (unilateral), the control limit includes either an upper control limit or a lower control limit for alarm monitoring. In an embodiment, the alarm monitoring strategy may include identifying patterns of out of control conditions. In another embodiment, the alarm monitoring strategy may include monitoring the trend in variable shifts.

Acquisition unit 406 may execute the following processes to determine the control limit of the control chart. In the following, UCL refers to the upper control limit, and LCL refers to the lower control limit.

For the single constant-type:
UCL=LCL=TARGET=a predetermined constant.

For the multi-level discrete type:
UCL=maximum constant value (e.g., the maximum value of the sample data),
LCL=minimum constant value (e.g., the minimum value of the sample data),
Target=mean value of the sample data.

For the continuous non-normal distribution type:
Target=average value of the sample data,
UCL=(100-p/2) percentile, LCL=(p/2) percentile, if the control chart is a non-normality bilateral control chart,
UCL=(100-p) percentile, or LCL=(p) percentile, if the control chart is a non-normal unilateral control chart, where p is the predetermined false alarm rate;

For the normal distribution type:
Target=sample data mean value u, $$u = \frac{\sum x_i}{N}$$

$$S = \sqrt{\frac{\sum (x_i - u)^2}{N-1}}$$

$$UCL = u + c \times S$$
$$LCL = u - c \times S$$

where:
$x_i$ is the sample data in the i-th data,
N is the number of the sample data,
UCL is the upper control limit,
LCL is the lower control limit,
c is an alarm rate adjustment factor. The alarm rate adjustment factor c can be obtained by solving the following equation:

$$1 - p\%/2 = \int_0^c \frac{1}{\sqrt{2\pi}} e^{\frac{x^2}{2}} dx$$

wherein p % is the predetermined alarm rate.

For the cyclical trend-up/down type and the drift after the PM type: the control limit can be determined based on a difference between two adjacent sample values of the sample data in accordance with the following expressions:

$$R = |x_i - x_{i-1}|$$

$$\overline{R} = \frac{\sum R_i}{N}$$

$$UCL = (1 + c \times 0.756) \times \overline{R}$$

where:
xi represents the i-th data in the sample data,
N represents the number of said sample data,
UCL is the upper control limit,
c is alarm rate adjustment factor. The alarm rate adjustment factor c can be obtained by solving the following equation:

$$1 - p\%/2 = \int_0^c \frac{1}{\sqrt{2\pi}} e^{\frac{x^2}{2}} dx$$

where p % is the predetermined alarm rate.

Monitoring unit 408 is configured to monitor the production process using the alarm monitoring strategy. In an embodiment, monitoring unit 408 includes a monitoring module configured to determine the control limit of the control chart for alarm monitoring of the process.

Figure 5:
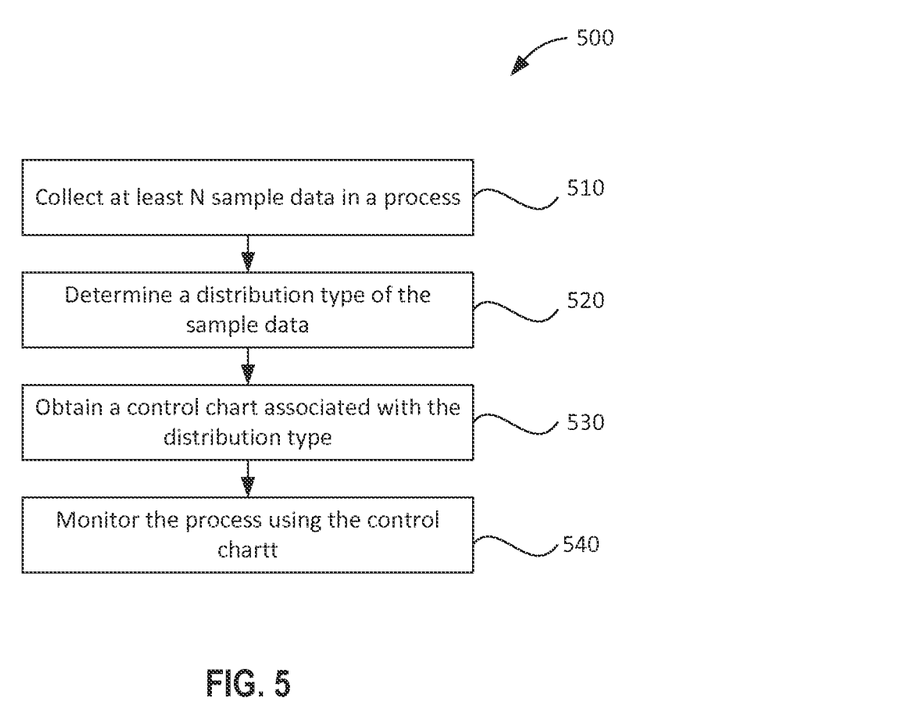
FIG. 5 is a flowchart diagram of a method according to some embodiments of the present invention.

FIG. 5 is a flowchart diagram of a method 500 according to some embodiments of the present invention. At 510, method 500 collects at least N sample data of a process. In an embodiment, collecting the sample data can be performed by hardware and/or software, or by a server that is coupled to a plurality of sensors configured to sense one or more parameters of a process. In an embodiment, the sample data is stored in a memory of the server. The server can be located at the proximity of the process to be monitored or remote from the process. At 520, the server may determine the distribution type of the sample data by executing program codes stored in a computer-readable storage medium or in a memory unit of the server. The sample data may be one of the many distribution types that have been described in sections above and won't be repeated herein for the sake of brevity. Method 500 also includes determining a predetermined range and removing sample data (outliers) that are located outside the predetermined range. In an embodiment, the range can be calculated as function of a 25 and a difference between the 75 and 25 percentiles adjusted by a scaling factor as described in sections above, so further description is omitted for the brevity reason.

At 530, method 500 further includes obtaining a control chart associated with the determined distribute type. The control chart can be a single-sided control chart or a two-sided control chart depending on the distribution type. Depending on the distribution type, the control chart may have an upper control limit and/or a lower control limit. The upper control limit can be a maximum value of the collect sample data in case that the distribution type is a normally distributed type or a multi-level discrete type. The upper control limit can be a function of a percentile such as (100−p/2) in the case of a two-sided control chart or (1−p) in the case of a single-sided control chart. Similarly, the lower control limit can be a minimum value of the collect sample data in case that the distribution type is a normal distribution type or a multi-level discrete type. The lower control limit can be a function of a percentile such as (p/2) in the case of a two-sided control chart or (p) in the case of a single-sided control chart. At 540, method 500 includes monitoring the process using the control chart.

Benefits and advantages of the present invention, and solutions to problems of alarm monitoring a production process have been described above with regards to specific embodiments. In the embodiments described above, through the selection of different control limits of the control charts for the different distribution types, the control limits for process control can be obtained quickly and accurately to indicate that a production process is out of a target specification or a machine is in need of adjustment or maintenance. Embodiments of the present invention are capable of reducing false alarm and effectively monitoring abnormal fluctuations of large amounts of data.

Those skilled in the art will appreciate that embodiments described above can be implemented using general-purpose computing devices (computers, servers), special purpose logic circuitry such as FPGA (field programmable gate array) or an ASIC (application specific integrated circuit). Modules can refer to portions of a computer program and/or processing units that implement that functionality. Processing units can refer to a single computing device or distributed in a network composed of multiple computing devices. Modules and processes can be implemented with a program code that is stored in a computer or machine-readable storage medium. The terms "modules" and "processes", as used herein, refer to, but are not limited to, software or hardware components that perform the tasks. For example, the alarm monitoring apparatus may be implemented on a computer having a display and/or acoustic device for displaying information to an operator or user. Other kinds of devices can be used for interaction with a user such as visual feedback, auditory feedback, tactile feedback.

The present invention has been described in terms of particular embodiments. The examples described herein are examples for illustration only and not intended to limit the present invention in any way. Those skilled in the art will appreciate that many modifications and alternatives are possible without departing from the teachings and advantages of this invention. Accordingly, any modifications, equivalent substitutions, improvements are intended to be included within the scope of the present invention.

What is claimed is:

1. A computer-implemented method for alarm monitoring of a process operation by an alarm monitoring apparatus comprising a sampling unit, a determining unit, an acquisition unit and a monitoring unit, the method comprising:
    collecting sample data representing one or more parameters of a process by the sampling unit;
    determining a distribution type of the sample data by the determining unit;
    obtaining an alarm monitoring strategy corresponding to the distribution type by the monitoring unit; and
    monitoring the process using the alarm monitoring strategy by the monitoring unit,
    wherein determining the distribution type of sample data comprises:
    determining whether a value level of the sample data is greater than a first threshold value;
    if the value level is not greater than the first threshold value, determining whether the distribution type is a single constant-type or multi-level discrete type; otherwise
    determining whether the sample data is normally distributed:
    if the sample data is normally distributed, setting the upper control limit to a maximum value of the sample data and the lower control limit to a minimum value of the sample data, and
    if the sample data is not normally distributed, determining whether the distribution type is a continuous non-normal distribution type, cyclical trend-up/down-type, or a drift after a periodic maintenance (PM) type.

2. The computer-implemented method of claim 1, wherein obtaining the alarm monitoring strategy comprises:
    determining a control limit of a control chart associated with the distribution type; and
    monitoring the production process using the control limit of the control chart.

3. The computer-implemented method of claim 1, wherein determining the distribution type further comprises:
    collecting at least a number N of the sample data, wherein N=2/p %, and p % is a predetermined alarm rate.

4. The computer-implemented method of claim 1, wherein determining whether the distribution type is a single constant-type or multi-level discrete comprises:
    if the value level is equal to 1 (unity), setting the control limit to a predetermined constant; otherwise,
    setting an upper limit of the control limit to the maximum value of the sample data;
    setting a lower control limit of the control limit to a minimum value of the sample data.

5. The computer-implemented method of claim 1, wherein determining the distribution type of the continuous non-normal distribution type, cyclical trend-up/down type, or drift after the PM type comprises:
    determining whether the distribution of the sample data satisfies PM changing conditions;
    if the sample data distribution does not satisfy the PM changing conditions, the distribution type is the continuous non-normal distribution type; otherwise,
    the distribution type is the cyclical trend-up/down type, or drift after the PM type.

6. The computer-implemented method of claim 5, wherein determining the continuous non-normal distribution type comprises:
    determining whether the control chart is a two-sided (bilateral) control chart;

if the control chart is the two-sided (bilateral control chart having an upper control limit (UCL) and a lower control limit (LCL), setting the UCL to (100−p/2) and LCL to (p/2); otherwise
setting the UCL to (100−p) or LCL to (p), wherein p is a predetermined alarm rate.

7. The computer-implemented method of claim 5, wherein determining the cyclical trend-up/down type or drift after the PM type comprises:
setting the control limit based on a difference between two adjacent sample values of the sample data, wherein the difference and an upper control limit of the control limit are computed using the following equations:

$$R = |x_i - x_{i-1}|$$

$$\overline{R} = \frac{\sum R_i}{N}$$

$$UCL = (1 + c \times 0.756) \times \overline{R}$$

wherein xi is an i-th data in the sample data, N is a number of the sample data, UCL is an upper control limit, c is an alarm rate adjustment factor,
wherein c is obtained by solving the following equation:

$$1 - p\ \%/2 = \int_0^c \frac{1}{\sqrt{2\pi}} e^{\frac{x^2}{2}} dx$$

wherein p % is a predetermined alarm rate.

8. The computer-implemented method of claim 5, wherein determining the distribution type comprises:
if the distribution type is determined to be the normal distribution type, and the control chart is a single-sided (unilateral) control chart having an upper control limit (UCL) or the lower control limit LCL, the UCL or the LCL is determined using the following expressions;
if the distribution type is determined to be the normal distribution type, and the control chart is a bilateral sided (bilateral) control chart having the upper control limit UCL and the lower control limit LCL, the UCL and the LCL are determined using the following expressions:

$$u = \frac{\sum x_i}{N}$$

$$S = \sqrt{\frac{\sum (x_i - u)^2}{N - 1}}$$

$$UCL = u + c \times S$$

$$LCL = u - c \times S$$

wherein xi is an i-th data in the sample data, N is a number of the sample data, c is an alarm rate adjustment factor,
wherein c is obtained by solving by the following equation:

$$1 - p\ \% = \int_0^c \frac{1}{\sqrt{2\pi}} e^{\frac{x^2}{2}} dx$$

wherein p % is the predetermined alarm rate.

9. An apparatus for alarm monitoring of a process operation, the apparatus comprising:
a sampling unit configured to obtain a number N of sample data representing one or more parameters in a production process;
a determining unit configured to determine a distribution type of the sample data;
an acquisition unit configured to acquire an alarm monitoring strategy for the distribution type; and
a monitoring unit configured to monitor the production process using the alarm monitoring strategy,
wherein the determining unit determines the distribution type of the sample data by performing following operations:
determining whether a value level of the sample data is greater than a first threshold value;
if the value level is not greater than the first threshold value, determining whether the distribution type is a single constant-type or multi-level discrete type; otherwise
determining whether the sample data is normally distributed:
if the sample data is normally distributed, setting the upper control limit to a maximum value of the sample data and the lower control limit to a minimum value of the sample data, and
if the sample data is not normally distributed, determining whether the distribution type is a continuous non-normal distribution type, cyclical trend-up/down-type, or a drift after a periodic maintenance type.

10. The apparatus of claim 9, wherein the number N is a function of a predetermined false alarm rate.

11. The apparatus of claim 9, wherein the determining unit removes outliers of the sample data located outside a predetermined range.

12. The apparatus of claim 9, wherein the acquisition unit determines a control limit of a control chart associated with the distribution type, the control limit having an upper control limit (UCL), a lower control limit (LCL), or both dependent upon whether the control chart is single-sided (unilateral) or two-sided (bilateral).

13. The apparatus of claim 9, wherein the sampling unit is further configured to determine whether the number N of sample data is below a predetermined value, if the number N is below the predetermined value, the sampling unit continues to obtain sample data until the number N of sample data is equal to or greater than the predetermined value.

14. The apparatus of claim 13, wherein the predetermined value is a function of a false alarm rate, an Alpha value, and a WECO rule.

15. A method for alarm monitoring abnormal conditions associated with a process operation by a server, the method comprising:
collecting at least N sample data representing one or more parameters of a process by the server;
determining a distribution type of the sample data by the server;
obtaining a control chart in response to the determined distribution type by the server; and
monitoring the process using the control chart by the server,
wherein N is a function of a predetermined false alarm rate p, and
wherein determining the distribution type of the sample data comprises:

determining whether a value level of the sample data is greater than a first threshold value;

if the value level is not greater than the first threshold value, determining whether the distribution type is a single constant-type or multi-level discrete type; otherwise determining whether the sample data is normally distributed:

if the sample data is normally distributed, setting the upper control limit to a maximum value of the sample data and the lower control limit to a minimum value of the sample data, and if the sample data is not normally distributed, determining whether the distribution type is a continuous non-normal distribution type, cyclical trend-up/down-type, or a drift after a periodic maintenance type.

16. The method of claim 15 further comprising:

removing outliers of the sample data located outside a predetermined range.

17. The method of claim 15, wherein the control chart comprises an upper control limit and a lower control limit if the distribution type is the multi-level discrete type or the continuous non-normal distribution type.

18. The method of claim 17, wherein the upper control limit is a maximum value of the sample data and the lower control limit is a minimum value of the sample data.

19. The method of claim 15, wherein the control chart is single-sided having an upper control limit equal to $(1-p)$ or a lower control limit equal to p.

20. The method of claim 15, wherein the control chart is two-sided having an upper control limit equal to $(1-p/2)$ and a lower control limit equal to $p/2$.

* * * * *